United States Patent [19]

Rind

[11] 4,356,821
[45] Nov. 2, 1982

[54] AIRWAY

[76] Inventor: Bruce Rind, 706 NE. 8th Ave., Aberdeen, S. Dak. 57401

[21] Appl. No.: 188,172

[22] Filed: Sep. 17, 1980

[51] Int. Cl.³ .................... A61M 16/00; A61M 29/00
[52] U.S. Cl. .................................. 128/207.14; 128/345
[58] Field of Search .................. 128/341, 345, 17, 18, 128/19, 20, 15, 200.26, 207.14, 12, 10

[56] References Cited

U.S. PATENT DOCUMENTS

| | | | |
|---|---|---|---|
| 1,097,978 | 5/1914 | Johnson | 128/17 |
| 1,275,520 | 8/1918 | Bell | 128/341 |
| 3,470,872 | 10/1969 | Grieshaber | 128/17 |
| 3,575,163 | 4/1971 | Gasper | 128/17 |
| 3,636,954 | 1/1972 | Weston | 128/321 |
| 4,263,898 | 4/1981 | Wannag | 128/17 |

*Primary Examiner*—Henry J. Recla

[57] ABSTRACT

An expandable airway for insertion into the throat of a patient having two elongated airway forming members each having a curved one-end portion adapted to fit the contours of the mouth and pharynx of a throat of a patient for effecting insertion and removal of the one-end portion of both into and out of the throat of a user. The two members are connected for pivotal movement in response to a force applied at the other end portions from a contracted state to at least one expanded state, wherein the one end portions are spaced apart relative to the contracted state. A holding member is disposed on the other end portion of one of said members for releasably holding the other of said members such that the members are maintained in said at least one expanded state and wherein said holding member is responsive to a force applied substantially in the direction of removal of the device from the throat to release the other of said members for free movement back to the contracted state.

16 Claims, 15 Drawing Figures

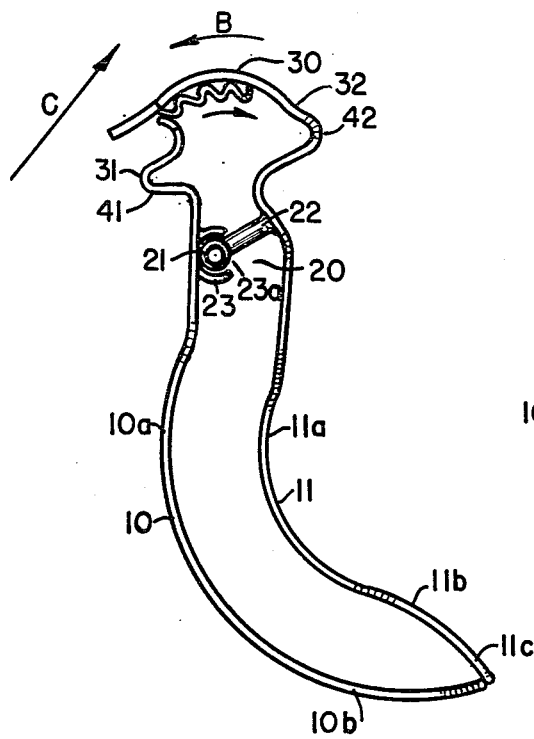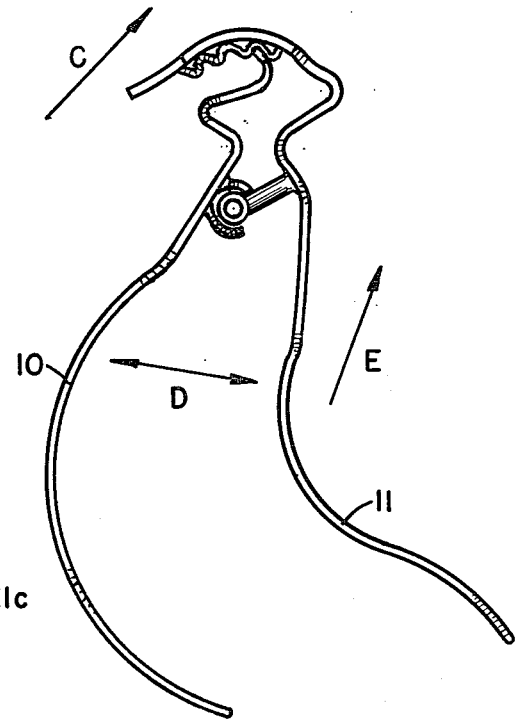
FIG. 1  FIG. 2
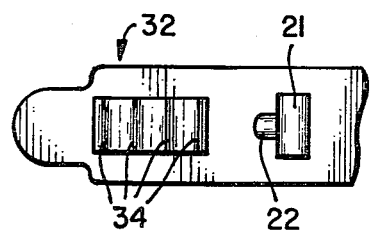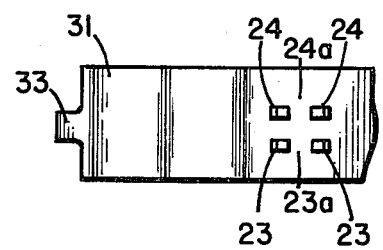
FIG. 3  FIG. 4

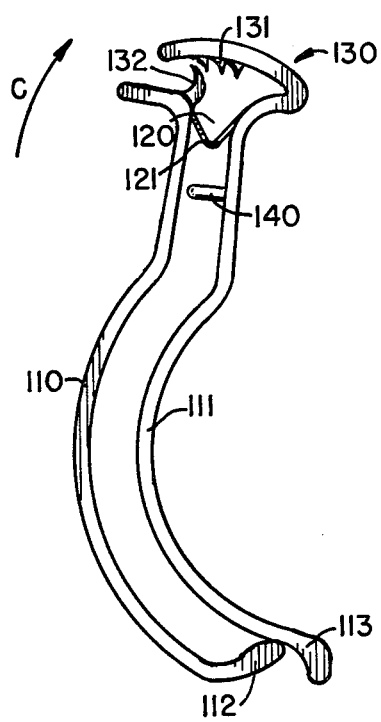
FIG. 5
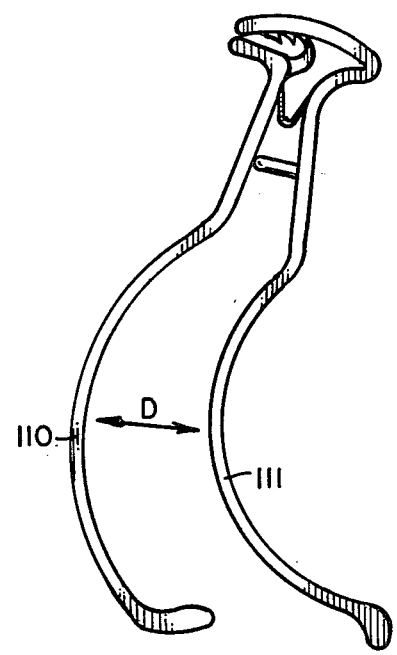
FIG. 6
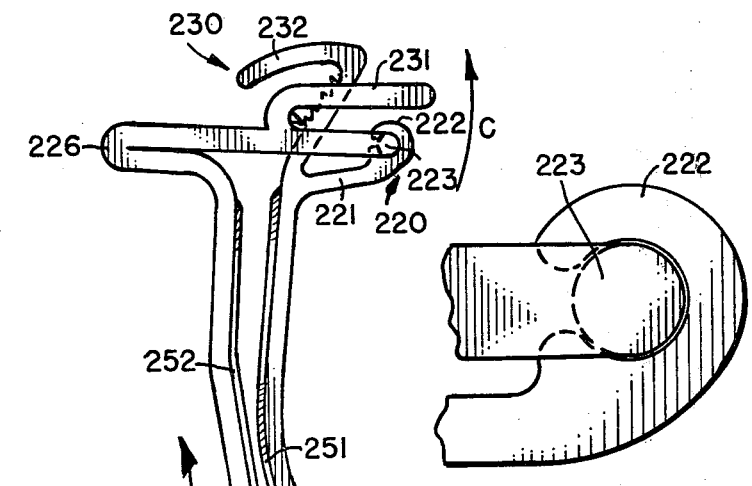
FIG. 7
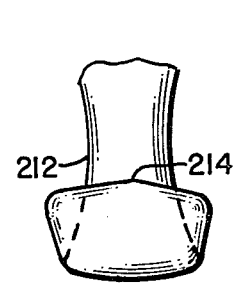
FIG. 11
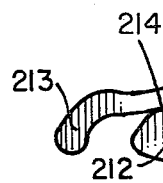
FIG. 9
FIG. 10

AIRWAY

BACKGROUND OF THE INVENTION

The present invention relates to an expandable airway which is a respiratory medical device for insertion in the mouth and pharynx to provide a passageway extending from a point adjacent to the tracheal orifice through the mouth opening through which air may enter and be expelled in breathing. An airway is particularly useful during surgery when a patient is under an anesthetic or in other situations where a person is unconscious by reason of which the pharynx is collapsed or obstructed so as to prevent natural respiration.

Conventional airways are generally of two types, a first type as disclosed in U.S. Pat. No. 2,599,521 constitutes a unitary member which is not adjustable in size, shape or contour and is made of a substantially rigid member which cannot be altered in use to fit particular patients, particular problems or particular changes in patient condition or position. A second is that shown for example in U.S. Pat. Nos. 2,127,215 and 3,930,507 which are adjustable and thus provide for expansion after insertion in the pharynx so as to tailor the device to a particular patient.

The aforementioned adjustable devices and the adjustable specula disclosed in U.S. Pat. Nos. 291,071, 350,809, 883,106, 1,388,421, 1,587,897 and 2,476,675, all have the disadvantage of not permitting an almost instantaneous and fail-safe removal of the airway during an emergency situation, since the mechanisms therefor are complex in nature and require a substantial amount of time for release. The adjustable airway disclosed in U.S. Pat. No. 3,930,507, while permitting a sliding motion to release same, also suffers from the problems of contracting unintentionally as a result of involuntary contractions on the part of the patient.

SUMMARY OF THE INVENTION

The main object of the present invention is to provide an expandable airway which eliminates the disadvantages of the prior art devices and which enables one to easily and quickly remove the airway from a patient in a fail-safe manner.

Another object of the present invention is to provide an airway which is easily insertable into the pharynx of a patient and which acts not only to depress the tongue, but is able to simultaneously place traction or pressure at the base (cephalad portion) to effect anterior motion of the epiglottis so as to open the air pressure for ventilation with a mask and for the insertion of an endotracheal tube or the like. This prevents a valve-like action of the epiglottis above the larynx which would result in an obstruction when air is forced in the direction of inhalation.

A further object of the present invention is to provide an expandable airway which has an end portion which is not only easily inserted into the pharynx of a patient but is also configured not to pinch the soft tissue in the pharynx during removal.

A still further object of the present invention is to provide an expandable airway which is also easily manufactured out of a single piece of plastic material and is therefore disposable and inexpensive to produce.

These and other objects of the present invention are achieved by the expandable airway according to the present invention which comprises two elongated airway forming members having a curved end portion for effecting insertion and removal thereof into and out of the throat of a user, means connecting the two members for pivotal movement in response to a force applied at the other end portions of the members from a contracted state to at least one expanded state wherein the curved end portions are spaced apart relative to the contracted state and means disposed on the other end portions of the two members for releasably maintaining the members in at least one expanded state and responsive to a force applied substantially in the direction of removal of the device from the throat to release the members for movement back to the contracted state.

The members are preferably pivotable to a plurality expanded states and are releasably maintainable in any one of the expanded states at a given time. The maintaining means is particularly commercially advantageously constructed as a one-way ratchet mechanism including first means forming ratchet teeth on one member and second means forming a pawl on the other member which is engageable with the ratchet teeth and wherein at least one of the first and second means is elastically deformable in response to a force in the removal direction to release the ratchet mechanism.

In order to enable the airway to be easily inserted, the termini of the two members abut in the contracted state and in order to prevent pinching of soft tissue, the termini of the two members are configured to abut along a single longitudinal line.

In order to effect the simultaneous depression of the tongue and the placing of traction at the cephalad base of the epiglottis to effect an anterior motion or a flipping of the epiglottis, the two members are connected by pivoting means which effects both relative rotation and longitudinal displacement thereof. This is particularly advantageously carried out by putting the pivot axis of the two members outside the members themselves or by effecting the pivot axis close to one of the two members.

In a particularly advantageous commercial embodiment of the present invention, the members comprise plastic material and a connecting means forms an integral plastic hinge connected between the two members and integral therewith.

The airway may also include a longitudinally extending strengthening rib along at least one surface of at least one member and means for spacing the members apart a predetermined minimum distance in the contracted state. In at least one embodiment, the spacing means includes the connecting means.

The structure of the expandable airway according to the present invention provides distinct advantages over the prior art. The connecting hinge when disposed between the two airway forming members is preferably narrower than the members themselves to prevent contact with soft tissues. In one particularly advantageous embodiment, the connecting means includes an integral hinge which comprises an inverted U-shaped member or a C-shaped member which enables the airway to be constructed as a one piece device. The device also has some "give" when the patient bites down and thus the bending adds a softness to the biting area even though the device is made out of a tough flexible plastic and thus diminishes the likelihood of damage to the teeth if the patient bites down hard while unconscious. Spacing means can be provided to limit the motion of the two members towards each other when the patient bites down hard as well as when the ratchet mechanism is squeezed for expansion.

The termini of the members are curved so as to not only allow easy entry into the mouth but to avoid damage to the mouth tissue when the members are expanded.

The space between the members is broad and unobstructed by any supporting structure and thus leaves an area in the oral cavity that is not only easy to work in such as for the purpose of suctioning out saliva, and gastric secretions but also permits the doctor to have a clear and unobstructed view into the oral cavity right through to the posterior pharynx. The anteriorly directed motion of the members, that is the longitudinal movement during pivoting, also helps in the elevation of the epiglottis by forces directed anteriorly at the base of the tongue thus flipping the epiglottis and moving it away from the trachea along with the pressure exerted downwardly which flips the epiglottis in the superior direction.

The ratchet mechanism of the present invention is particularly advantageous in view of the qualities that are necessary for an airway device, since the function of the airway is not only to maintain an oropharyngeal airway while the patient is unconscious but to separate the teeth so that the patient will not bite on an endotracheal tube and thus obstructing what may be the patients' only airway at the time. Also, in a case where the necessity arises for the rapid removal of the airway from the mouth, such as what happens when the patient begins to gag on it as he regains consciousness or vomits from gagging or for some other unforeseen reason, it is necessary to be able to effect this rapidly, without the need to release any complicated mechanism which would be time consuming such as a screw or a snap which cannot be released with a gentle force or a mechanism that requires release by a force having a the direction contrary to the direction of removal from the mouth. The ratchet mechanism of the present invention, by utilizing the elastic deformability of the means forming the ratchet mechanism, enables one to pull the airway out of the mouth and at the same time enable the release of the traction mechanism thus allowing the airway to contract and thus exit from the mouth easily. The ratchet mechanism must also be simple with a minimum number of moving parts, the reason being that the simpler it is, the less likelihood of a breakdown during use. The elimination of the possibility of breakdown is not only for convenience, but rather is necessary for the safe operation of the airway, since the device is used when the mouth is open and the patient is lying on his back and therefore a loose or broken piece from the airway might fall into the mouth and be aspirated thus endangering the patient's life. A mechanism must also be used such that the likelihood of jamming is minimal since it can be fatal if there is any difficulty either in the opening or the closing thereof. Another important aspect of the rachet mechanism is that it must be small enough so as to not prevent the placement of an oxygen mask over the mouth and nose, yet it should be of sufficient size to rest on the outer mouth so as to prevent the airway from slipping too far into the mouth.

The ratchet mechanism according to the present invention has the advantages of enabling the airway to maintain the separation of the upper and lower teeth, provide a quick and easy release without jamming and in an uncomplicated manner, is sturdy and stable enough to maintain the traction position and has few if any movable parts to minimize the possibility of breakdown.

These and other objects and advantages of the invention will become apparent when viewed with the drawings which show various embodiments of the invention by way of example wherein:

BRIEF DESCRIPTION OF THE DRAWINGS

FIG. 1 is a side view of the first embodiment according to the present invention;

FIG. 2 is a side view of the embodiment of FIG. 1 in an expanded state;

FIG. 3 is a bottom view of one portion of the rachet assembly;

FIG. 4 is a side view of another portion of the rachet assembly of FIG. 1;

FIG. 5 is a side view of another embodiment according to the present invention;

FIG. 6 is a side view of the embodiment of FIG. 5 shown in an expanded state;

FIG. 7 is a side view of another embodiment according to the present invention;

FIG. 9 is a detailed side view of the pivot connection of the embodiment of FIG. 7;

FIG. 10 is a top view of the pivot connection of the embodiment of FIG. 7;

FIG. 11 is a front view of the terminus of one of the members of FIG. 7;

DETAILED DESCRIPTION OF THE INVENTION

Figure 8:
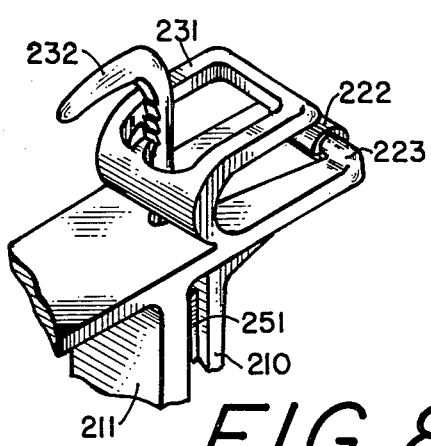
FIG. 8 is a top perspective view of the rachet assembly of the embodiment of FIG. 7.

Referring now to FIGS. 1-4, a first embodiment of the present invention is shown. The airway comprises airway forming members 10, 11 which are pivotally connected by means 20. The members 10, 11 include a substantially arcuate first section which conforms to the shape of the pharynx and end portions 10b, 11b. As shown in FIG. 1, the end portion 11b has an oppositely curved portion 11c which curves towards the member 10 so as to gradually taper and abut end portion 10b of member 10 when the airway is in the contracted state shown in FIG. 1.

The members 10, 11 comprise substantially planar members in the curved configuration and can be made out of a metal or out of a substantially rigid plastic. As a result of the configuration of members 10 and 11, these members form an airway therebetween and when put into the expanded state shown in FIG. 2, provide an entirely unobstructed path from the mouth orifice.

The pivotal connecting means 20 in the embodiment shown in FIGS. 1-4 comprises a pivot rod 21 which is rigidly fastened via neck portion 22 to the member 11 and spaced therefrom. The pivot rod 21 is seated in means forming a pivot slot which comprises members 23 and 24 which are generally ring-shaped members having an open wall portion 23a, 24a and which deform to receive the rod 21 therein for rotational movement within the members 23, 24. To assemble the device, the rod 21 is snapped into place into members 23, 24 through open wall portions 23a, 24a by a manual force in the inward direction. Because of the generally inward direction of the forces applied on the device during the use of the airway, the pivot means will not inadvertently separate.

The members 10 and 11 are shown in the contracted state in FIG. 1 with the end portions 10b, 11b preferably abutting and tapered to the termini thereof so as to enable the easy insertion of the airway into the pharynx. Since during the use of the airway it is desirable to adjust the size of the airway to the particular patient or a particular condition of a patient, the members 10 and 11 are pivotable about pivot means 20 to move from the contracted state shown in FIG. 1 to any one of a plurality of expanded states as for example shown in FIG. 2. In order to maintain the members 10, 11 in the expanded state, a maintaining means 30 is provided. The maintaining means 30 includes a portion 31 on member 10 and a portion 32 on member 11. More specifically, the maintaining means comprises a ratchet mechanism with the portion 31 comprising means forming a pawl 33 and the portion 32 including means forming ratchet teeth 34. The pawl 33 engages with the individual ratchet teeth 34 so as to slide in direction A without any resistance, however it locks in direction B as a result of the engagement of the pawl 33 and a given ratchet tooth 34. Equally important is the fact that the means forming either or both of the portions 31 and 32 of the ratchet mechanism are elastically deformable in a direction C which is substantially the direction of removal of the device from the pharynx. As shown in FIG. 2, the deformation of the portion 32 in response of the removal of the airway in the direction C, acts to release the pawl 33 from the teeth 34 thus permitting the airway to move from the expanded state shown in FIG. 2 to the contracted state shown in FIG. 1 and thus enable the removal thereof without any further manipulations.

It should also be noted that the pivot means 20 is constructed so that the pivot rod 21 is closer to member 10 than to member 11. This intentional positioning of the pivot axis is carried out to produce a simultaneous angular displacement D and longitudinal displacement E when the members are moved from the contracted state shown in FIG. 1 to the expanded state shown in FIG. 2. The purpose of the dual displacement, is to effect the simultaneous depression of the tongue and the anterior pulling at the base of the tongue to pull and thereby elevate the epiglottis in order to further clear the trachea.

The members 10 and 11 also include widened portions 41, 42 respectively which act to prevent the inadvertent sliding of the airway into the mouth during use.

Further, it is important that the airway not be permitted to contract any further than that shown in the contracted state of FIG. 1 and as a result, spacing means may be utilized to ensure this. In the embodiment shown in FIG. 1, the spacing means includes the pivot means 20 which acts to prevent any movement of the members towards one another and the tapering of end portion 11c which abuts on member 10 at the end thereof also acts to space the members 10 and 11 apart by a given minimum distance.

FIGS. 5 and 6 show a second embodiment of the present invention which utilizes the same principles as that of the embodiment of FIGS. 1-4, but has the preferred advantage of being capable of being constructed out of a single integral piece of plastic material.

In this embodiment, the pivot means 120 comprises a U-shaped member 121 which is integral with the members 110, 111 and is capable of elastically and deformably bending to permit the expansion of the members 110, 111 from the contracted state shown in FIG. 5 to the expanded state shown in FIG. 6. The releasable maintaining means 130 also comprises a ratchet mechanism similar to that of the embodiment of FIGS. 1-4, however made entirely of one piece as shown. The means 131 forming the ratchet teeth is deformable in the direction C of removal of the device to release the teeth from the pawl 132.

This embodiment also differs from that of the first embodiment in the configuration of the termini 112, 113 of the members 110, 111. As shown, the termini 112, 113 diverge from the curve of the arcuate portions of the members 110, 111 so that the portion 112 abuts member 111 when the device is in the contracted state and the portion 113 slightly overlaps portion 112 so as to form a tapering configuration to enable the ease of insertion into the pharynx. Moreover, the end portions 112, 113 are rounded at their tips and have a widened end portion to prevent tissue damage during insertion. Finally, portion 113 is configured to favorably act on the base of the tongue so as to more reliably effect the elevation of the epiglottis during expansion.

As a result of the fact that the connecting means 120 comprises the elastically deformable U-shaped member 121, it is desirable to provide spacing means to prevent the complete contraction of the device in response to the unconscious biting down of the patient when the airway is inserted in the pharynx. Thus spacing member 140 is provided on member 111 which is slightly spaced at its end portion from member 110 so as to enable a slight amount of give in response to the clamping down on the device by a patient so as to prevent the breaking of teeth at that time. However, upon the deformation inwardly of the member 121 in response to the closing of the mouth by a patient, the member 140 will contact member 110 and prevent any further contractions thus defining the minimum spacing between members 110 and 111.

It should also be noted that the connecting member 121 and the spacing member 140 have a width which is narrower than the width of the members 110 and 111 so as to prevent the possibility of pinching soft tissue during the insertion of the airway into the pharynx.

FIGS. 7-11 show a third embodiment of the present invention which also utilizes the key features of the present invention as has been already been explained with respect to the other embodiments. As shown, the members 210, 211 include stiffening ribs 251, 252 on the inner surfaces thereof which act to strengthen the members and prevent the deformation thereof and also act as spacing means to prevent the members from contracting more than a predetermined amount defined by the thickness of the strengthening ribs.

The end portions 212, 213 of the members 210, 211 are similar to that of the embodiment of FIGS. 5 and 6, except that the embodiment herein as shown in FIG. 11 has a tapered portion on end portion 212 which crests at a single substantially central line 214 so that when member 210 abuts against member 211 in the contracted state shown in FIG. 7, the abutment is only along a line to prevent the pinching of soft tissue when the device is released and moves from the expanded state to the contracted state for removal.

It should be clear to those skilled in the art that this type of configuration for the termini of the airway forming members could be utilized in the embodiments of FIGS. 1-8 and 12-13 that such modification is within the scope and intent of this invention.

In this embodiment, the pivoting means 220 is configured so as to define a pivot axis outside the two members 210, 211 so as to increase the degree of longitudinal displacement in the direction E of the members during the angular displacement from the contracted state to the expanded state and thus improve the action of the airway on the epiglottis.

As shown, the pivot means 220 has the dual function of also defining the widened portion which prevents the inadvertent sliding of the airway into the pharynx during use. Member 221 extends substantially perpendicularly to member 210 and has an end portion 222 at the end thereof defining a slot for receiving pivot rod 223 which is connected by members 224 and 225 to connecting member 226 which is substantially perpendicular to member 211. Thus members 226 and 221 form the portion which prevents insertion into the mouth.

As shown in FIG. 9, end portion 222 is slotted and deforms to receive pivot rod 223 therein for rotational movement.

The ratchet mechanism shown in FIGS. 7 and 8 includes ratchet tooth forming member 232 and pawl forming member 231. As is clear, member 231 is deformable in direction C to release the pawl from the ratchet teeth to effect removal of the device from the pharynx.

Figure 12:
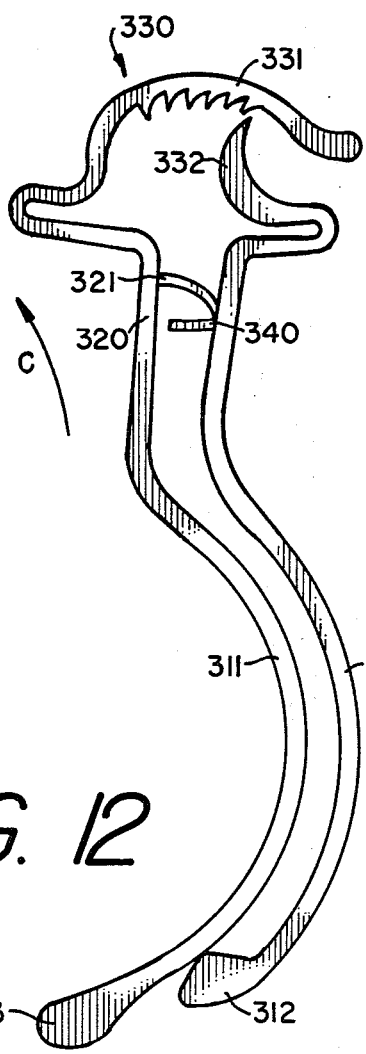
FIG. 12 is a side view of another embodiment according to the present invention.

FIG. 12 shows a fourth embodiment of the invention wherein members 310 and 311 have end portions 312 and 313 similar to that of the embodiment shown in FIGS. 7-11. The embodiment of FIG. 12 includes the connecting means similar to that of the embodiment of FIGS. 5 and 6, however, instead of having the inverted U-shaped member shown therein, the connecting means includes an arcuate member 321 integral with members 310 and 311 and of a lesser width, but which by its configuration enables the angular displacement in the direction B and the longitudinal displacement in the direction E which is found to be desirable. Thus the embodiment of FIG. 12 combines the advantages of the integral construction of the embodiment of FIGS. 5 and 6 with the ability for longitudinal displacement and thus elevation of the epiglottis of the embodiment of FIGS. 1-4.

The embodiment of FIG. 12 also includes the spacing member 340 which acts similar to that of member 140 in the embodiment of FIGS. 5 and 6.

The releasable rachet mechanism 330 is formed by member 331 which forms the teeth and member 332 which forms the pawl. As can be clearly seen from the embodiment shown, the member 331 is deformable in the direction C of removal and thus will act to release the pawl 332 from the teeth as heretofore explained.

Figure 13:
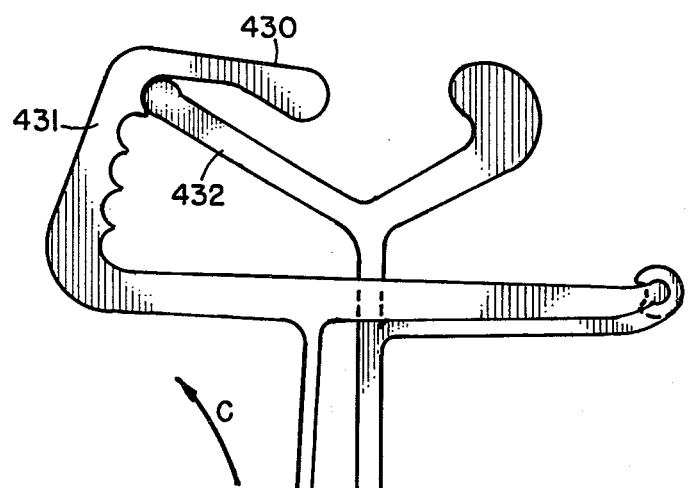
FIG. 13 is a side view of a still further embodiment according to the present invention.

FIG. 13 shows a still further embodiment wherein the end portions 412, 413 of members 410 and 411 are similar to those of the embodiment of FIGS. 5 and 6 and the pivot means 420 is similar to that discussed with respect to the embodiment of FIGS. 7-11. In this embodiment, the ratchet mechanism 430 is slightly different and includes the portion forming rachet teeth 431 in the portion forming the pawl 432. As can be clearly seen, the member 431 is deformable in the direction C to effect release of the ratchet mechanism during removal. This embodiment also includes spacing members 440 to define a minimum spacing.

Figure 14:
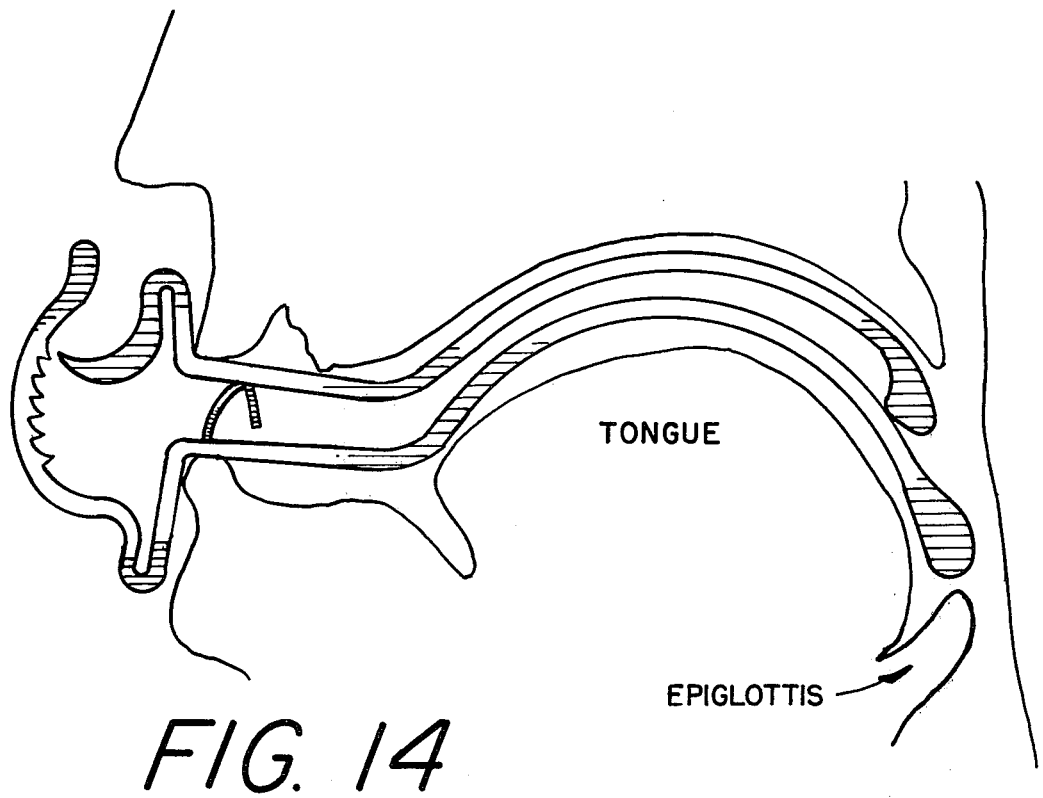
FIG. 14 shows the embodiment of FIG. 12 in the contracted state in the mouth.
Figure 15:
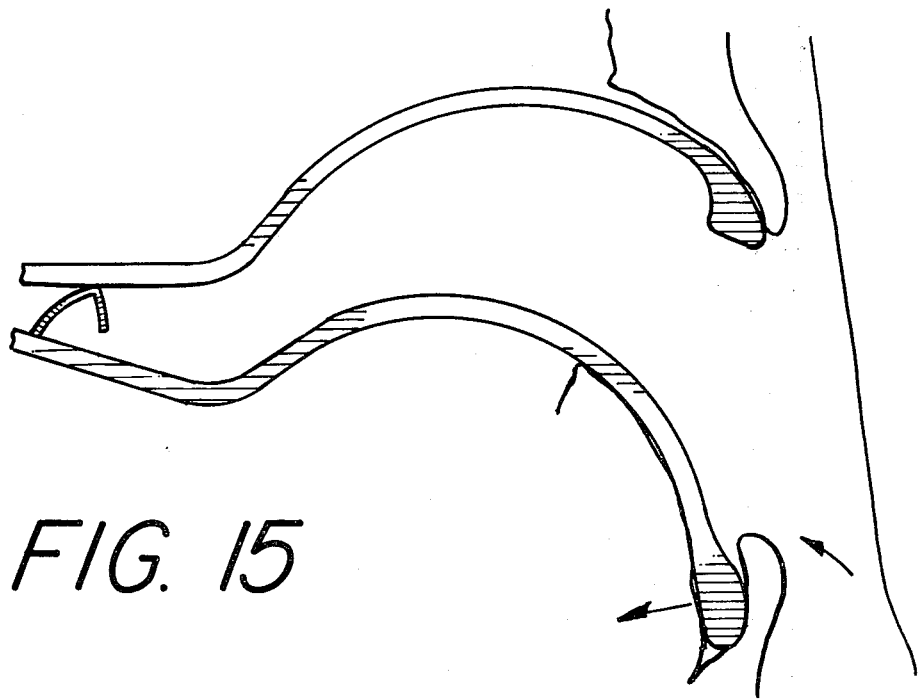
FIG. 15 shows the airway of FIG. 12 in an expanded state in the mouth.

FIGS. 14 and 15 show the insertion of the embodiment of the invention shown in FIG. 12 in the pharynx. FIG. 14 shows the insertion of the device and its position in the pharynx in the contracted state while FIG. 15 shows the position of the pharynx when the airway is in the expanded state. As can be clearly seen, the longitudinal displacement effected by the pivot means 20 pulls the base of the tongue so as to elevate the epiglottis and provide a clear path into the trachea.

It will be appreciated that the instant specification and claims are set forth by way of illustration and not lmitation, and that various modifications and changes may be made without departing from the spirit and scope of the present invention.

What is claimed is:

1. An expandable oral airway for insertion into the throat of a patient comprising:
   two elongated airway forming members each having a curved one-end portion adapted to fit the contours of the mouth and pharynx of a throat of a patient for effecting insertion and removal of the one end portion of both into and out of the throat of a user;
   means connecting the two members for pivotal movement in response to a force applied at the other end portions of the members from a contracted state to at least one expanded state, wherein the one end portions are spaced apart relative to the contracted state; and
   holding means disposed on the other end portion of one of said members for releasably holding the other of said members such that the members are maintained in said at least one expanded state and wherein said holding means is responsive to a force applied substantially in the direction of removal of the device from the throat to release the other of said members for free movement back to the contracted state.

2. The airway according to claim 1, wherein the members are pivotable to a plurality of expanded states and the holding means releasably maintains the members in any one of the plurality of expanded states at a given time.

3. The airway according to claim 2, wherein the holding means comprises a one-way ratchet mechanism including first means forming ratchet teeth on one member and second means forming a pawl on the other member engageable therewith and wherein at least one of the first and second means is elastically deformable in response to a force in the removal direction to release the rachet mechanism.

4. The airway according to claim 1, wherein the connecting means effects simultaneous relative rotational and longitudinal displacement of the two members.

5. The airway according to claim 1 or claim 4, wherein the connecting means comprises a pivot pin connected to one member and means forming a pivot slot connected to the other member and receptive of the pivot pin therein for rotational movement.

6. The airway according to claim 5, wherein the pivot pin and pivot slot are disposed between the two members.

7. The airway according to claim 5, wherein the pivot pin and pivot slot are disposed outside the two members.

8. The airway according to claim 1 or claim 4, wherein the members comprise plastic material and wherein the connecting means comprises means forming an integral plastic hinge connected between the two members and integral therewith.

9. The airway according to claim 1, wherein at least one of said members has a longitudinally extending strengthening rib along one surface thereof.

10. The airway according to claim 1, further comprising means for spacing the members apart a predetermined minimum distance in the contracted state.

11. The airway according to claim 10, wherein the spacing means includes the connecting means.

12. The airway according to claim 1, wherein the one end portions of the two members are configured in the closed state to be gradually closer towards the termini thereof.

13. The airway according to claim 12, wherein the termini of the two members abut in the contracted state.

14. The airway according to claim 13, wherein the termini of the two members are configured to abut along a single substantially central longitudinal line to prevent pinching of tissue.

15. An expandable airway comprising:
two elongated oral airway for insertion into the throat of a patient forming members each having a curved one-end portion adapted to fit the contours of the mouth of a patient for effecting insertion and removal of the one end portion of both into and out of the throat of a user;
means connecting the two members for pivotal movement in response to a force applied at the other end portions of the members from a contracted state to at least one expanded state, wherein the one end portions are spaced apart relative to the contracted state;
means disposed on the other end portions of the two members for releasably maintaining the members in said at least one expanded state; and
wherein the termini of the two members are configured to abut along a single substantially central longitudinal line to prevent pinching of tissue.

16. The airway according to claim 15, wherein the one end portions of the two members are configured in the closed state to be gradually closer towards the termini thereof.

* * * * *